United States Patent [19]
Nielsen

[11] Patent Number: 5,158,572
[45] Date of Patent: Oct. 27, 1992

[54] MULTIFOCAL INTRAOCULAR LENS

[76] Inventor: James M. Nielsen, 2339 Sunset Point Rd., Suite 300, Clearwater, Fla. 33575

[21] Appl. No.: 95,360

[22] Filed: Sep. 10, 1987

[51] Int. Cl.⁵ ............................................. A61F 2/16
[52] U.S. Cl. ...................................... 623/6; 351/161; 351/168
[58] Field of Search ........................... 623/4–6; 351/161, 168

[56] References Cited

U.S. PATENT DOCUMENTS

| | | | |
|---|---|---|---|
| 4,170,043 | 10/1979 | Knight et al. | 623/6 |
| 4,402,579 | 9/1983 | Poler | 623/6 X |
| 4,636,211 | 1/1987 | Nielsen et al. | 623/6 |
| 4,704,016 | 11/1987 | DeCarle | 351/161 |
| 4,813,955 | 3/1989 | Achatz et al. | 623/6 |

FOREIGN PATENT DOCUMENTS

| | | |
|---|---|---|
| 0140063 | 5/1985 | European Pat. Off. |
| WO86/03961 | 7/1986 | PCT Int'l Appl. ............ 623/6 |

*Primary Examiner*—Ronald Frinks
*Attorney, Agent, or Firm*—Lyon & Lyon

[57] ABSTRACT

Multifocal lenses are formed having a substantially circular central region having a first optical power, surrounded by a plurality of concentric ring regions which alternate between at least two optical powers, one of which may be the first optical power. Preferably, the central region is powered for near vision. For example, one embodiment of the invention is a bifocal lens having a central near-vision portion, a first concentric ring region powered for distance vision, and a second concentric ring region having the same power as the central region.

18 Claims, 2 Drawing Sheets

MULTIFOCAL INTRAOCULAR LENS

BACKGROUND OF THE INVENTION

The present invention relates to a multifocal intraocular lens for implantation in the human eye having a plurality of concentrically-arranged regions alternately powered for differing vision ranges, e.g., near and far vision, surrounding a substantially circular central region.

Various lenses have been disclosed which have a circular central region surrounded by a single ring. For example, U.S. Pat. No. 3,420,006 discloses bifocal contact lenses in which a central region powered for distance vision is surrounded by a ring powered for near vision, while U.S. Pat. No. 3,270,007 discloses the reverse configuration. U.S. Pat. Nos. 3,726,587 and 4,636,049 also disclose bifocal contact lenses in which a central region powered for near vision is surrounded by a ring powered for far vision. These latter lenses are said to work better than earlier lenses having the near-vision portion outside the distance portion.

U.S. Pat. No. 4,573,775 discloses soft multifocal contact lenses having a vertical array decreasing power. U.S. Pat. No. 4,580,882 discloses a contact lens in which the power varies continuously outward from a central area for distance vision.

U.S. Pat. No. 4,636,211 discloses bifocal intraocular lenses having a central region powered for near vision and a single surrounding ring powered for distance vision.

Each of these earlier disclosures offers some optical theory as to the reason for operation of a particular lens design, and U.S. Pat. Nos. 3,726,387, 4,636,049 and 4,636,211 specify particular preferred sizes for the near and far vision portions. Such size specifications represent a compromise, however, in order to provide adequate light collecting area in both the far and near vision segments if significant pupillary excursion occurs under different lighting conditions. This compromise is necessary if the known lenses are to provide both distance and near vision at both extremes of high and low lighting levels and thus small and large pupillary aperature, but leads to decreased efficiency of near vision at low lighting levels (assuming a near-vision central portion) and decreased efficiency for far vision at high light levels. The claimed invention overcomes this difficulty, thus providing bifocal intraocular lenses which more closely approximate the vision range of a natural lens.

SUMMARY OF THE INVENTION

According to the invention, multifocal lenses are formed having a substantially circular central region having a first optical power, surrounded by a plurality of concentric ring regions which alternate between at least two optical powers, one of which may be the first optical power. Thus, the concentric ring regions begin with an innermost ring region having a power different from the power of the central region, and progress outward with each successive ring region having a power different from the power of the immediately inward ring region, with the proviso either that a least one of the ring regions has the same power as the central region, or that at least two of the ring regions have the same power. Preferably, the central region is powered for near vision. For example, one embodiment of the invention is a bifocal lens having a central near-vision portion, a first concentric ring region powered for distance vision, and a second concentric ring region having the same power as the central region.

DETAILED DESCRIPTION OF THE INVENTION

Figure 1:
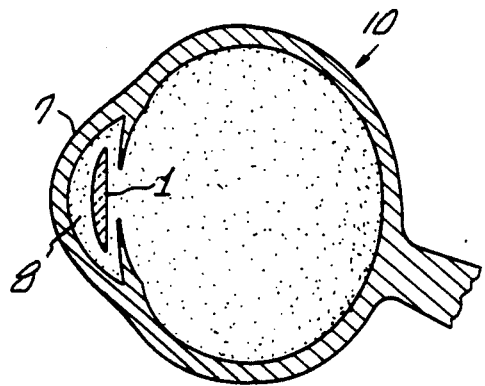
FIG. 1 shows a sectional view of a human eye with the intraocular multifocal lens implanted in the anterior chamber.
Figure 2:
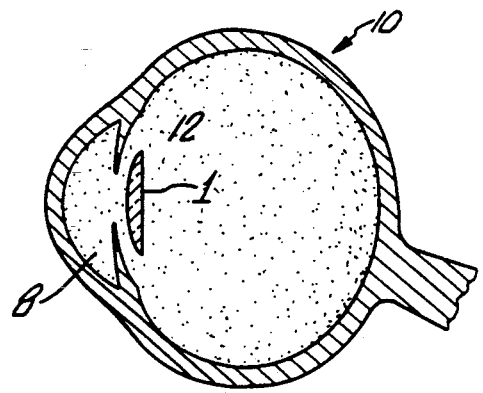
FIG. 2 shows a sectional view of a human eye with the intraocular lens implanted in the posterior chamber.

Intraocular lenses are surgically implanted lenses used as a replacement for, or in some cases as an adjunct to the natural lens. For example, after a cataract or clear lens extraction operation in which the natural lens is removed, an intraocular lens may be implanted in either the anterior chamber 8 or the posterior chamber 12 of the human eye 10 as shown in FIGS. 1 and 2 respectively. In either case, the lens may be affixed in place using any of a wide variety of haptic designs which are well known in the art.

Figure 3:
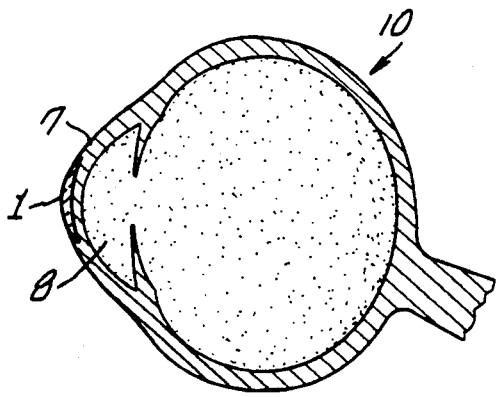
FIG. 3 shows a sectional view of a human eye with an intraocular multifocal lens permanently fixed on the cornea beneath the epithelium.
Figure 4:
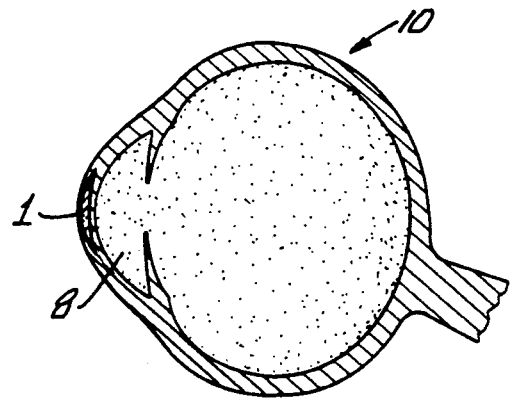
FIG. 4 shows a sectional view of a human eye with an intraocular multifocal lens permanently fixed in the cornea in the stroma layer.
Figure 5:
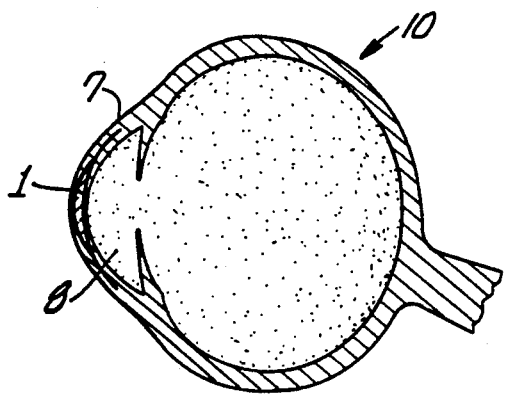
FIG. 5 shows a sectional view of a human eye with an intraocular multifocal lens permanently fixed in a pocket in the cornea between the epithelium and endothelium.

Intraocular lenses may also be implanted by corneal-inlay techniques, i.e., they may be surgically placed in various positions in or on the cornea 7. FIGS. 3-5 exemplify these various positions within the cornea; i.e., just below the epithelial layer (FIG. 3), within the stroma layer (FIG. 4), and within the cornea in a surgically created pocket (FIG. 5). The intraocular lens according to the invention may advantageously be utilized in any of these environments.

Figure 6:
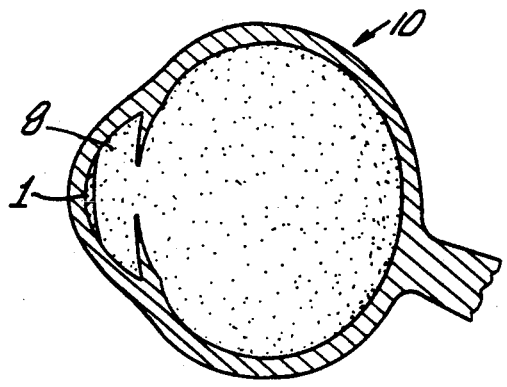
FIG. 6 is a plan view of an intraocular bifocal lens according to the invention.

FIG. 6 shows one embodiment of a bifocal intraocular lens according to the invention. This lens 1 has a substantially circular central region 22, a first concentric ring region 24 coaxially surrounding the central region 22, and three more concentric ring regions 26, 28 and 30 coaxially surrounding the first concentric ring region 24. If the central region 22 is powered for near vision, then concentric ring regions 24 and 28 are powered for far vision, while concentric ring regions 26 and 30 are powered for near vision. In this way, an alternating pattern of near-far-near-far-near is obtained in the central and ring regions of the lens. In other embodiments of the invention, fewer or more concentric ring regions might be used. In addition, rings having additional powers may be incorporated in an alternating fashion to give a multifocal lens. In a multifocal lens, the concentric ring segments may be an alternating array of regions of two or more powers all of which are different from the power of the central circular region. Alternatively, the ring segments may include rings of the same power as central circular region, along with ring segments of two additional powers. Thus, for example, in a trifocal lens having lens powers designated A, B, and C, the concentric rings might be arrayed as B-C-B, B-C-B-C, B-C-A-B, or B-C-A-B-C around a central circular portion of power A. An example of B-C-A-B-C is shown in FIG. 6 as respective concentric rings 24, 25, 28, 30 and 31.

Figure 7:
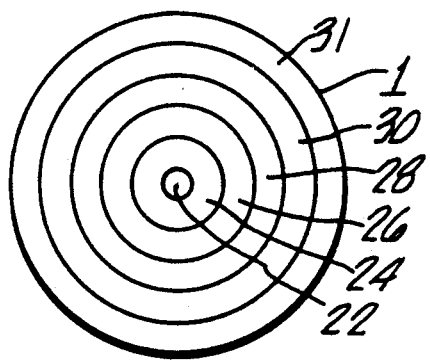
FIG. 7 shows a sectional view of the intraocular lens having a plano-convex shape.
Figure 8:
FIG. 8 is a sectional view of the intraocular multifocal lens having a bi-convex shape.
Figure 9:
FIG. 9 shows a convex-plano-convex lens.
Figure 10:
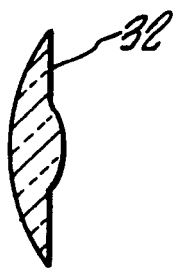
FIG. 10 shows a convex-concave intraocular lens.
Figure 11:
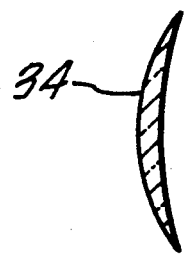
Figure 1:
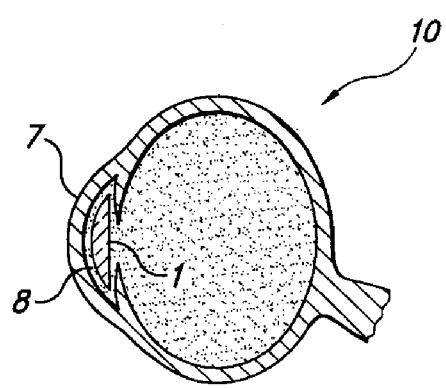
Figure 2:
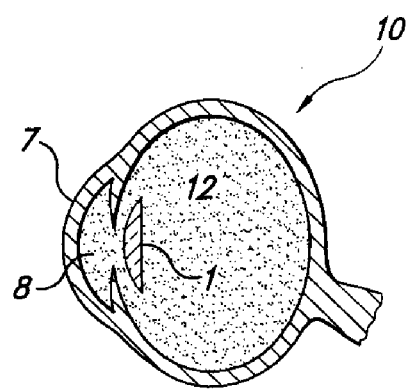
Figure 3:
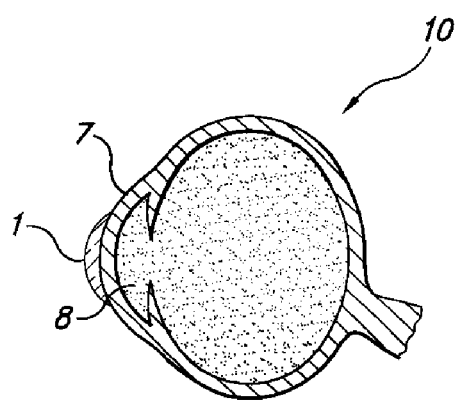
Figure 4:
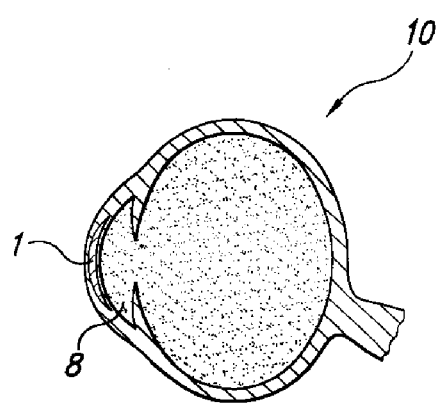
Figure 5:
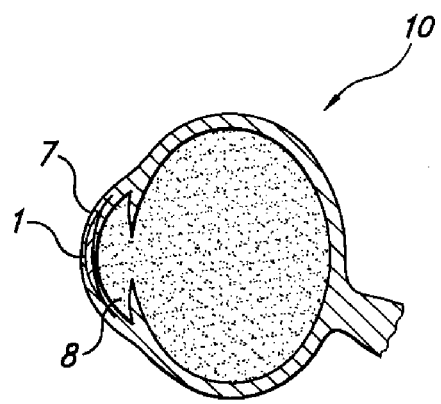
Figure 6:
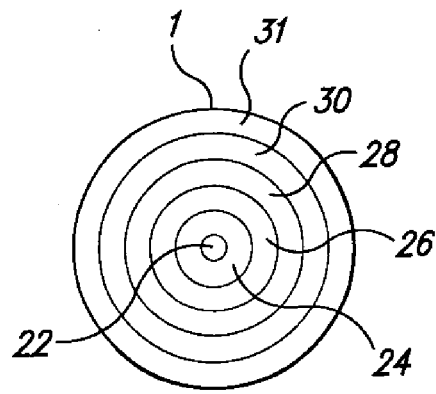
Figure 7:
Figure 8:
Figure 9:
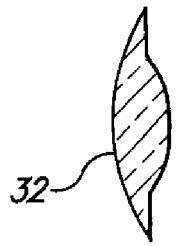
Figure 10:
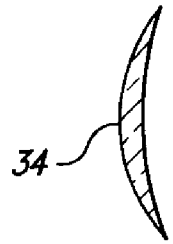

The intraocular lens according to the invention advantageously may have a plano-convex shape (FIG. 7) or a bi-convex shape (FIG. 8). In addition, lenses according to the invention may have a convex-concave shape (FIG. 10) or a convex-plano-convex shape (FIG. 9) or a biconcave shape.

Pseudophakic eyes generally exhibit less pupillary excursion than average, due to the general tendency for this type of surgery to be performed on elderly patients who exhibit varying degrees of senile miosis. In addition, some degree of miotic behavior may be the result of the surgery itself. Nevertheless, some degree of pupillary excursion due to differing lighting conditions and the normal accommodation for close focusing occurs in many patients. The lenses according to the invention provide superior vision of both near and far objects throughout the range of pupillary excursion. This is achieved by selecting the relative sizes of the regions such that as the pupillary aperture changes the portion of a bifocal lens exposed always has about one-half of the pupillary area powered for near vision and the other half powered for far vision. In a multifocal lens having three or more powers, the relative areas are similarly balanced to achieve optimum light transmission for segments of each power under all conditions.

In practice, this can be achieved with a lens having an overall diameter of about 6 to 7 mm in which the central region is from 1 mm to 3 mm and the concentric ring regions have a radial thickness of about 0.125 mm or more. Given the normal diameter for the lens, the maximum radial thickness of any one ring region is about 2 mm. The rings can differ in radial thickness, for example by becoming successively narrower so that the area of the rings is constant, or the radial thickness of the rings can be kept constant. The eye size and extent of pupillary excursion in an individual patient should be considered in establishing the actual dimensions of a lens.

The lenses according to the invention provide multifocal vision by relying upon the nervous system's inherent ability to selectively perceive one of two or more sets of optical inputs, e.g., near and far objects. In order for adequate differentiation and rapid neurotransfer between the two sets of inputs to be achieved, a difference in effective power of at least 2.5 diopters is generally necessary although this will vary somewhat from patient to patient. Some patients may achieve effective neurotransfer with differences as low as 1 diopter, while others may require differences as large as 3 diopters. In additional corneal inlay usage will require a lesser difference because of the increased distance from the retina.

The actual powering of the far and near vision regions is selected based on the needs of the individual patient, but the average patient will require a power of +10 to +30 diopters in the far vision regions of the lens, and a power of +10 to +40 diopters in the near vision region of the lens.

The lenses according to the invention can be fabricated by lathe cutting, compression or injection molding, photoetching, milling or electro-forming. The near optic may be placed on either surface of the lens with the power corrected accordingly. Similarly, the concentric ring regions may be formed by varying the curvature of concentric ring portions on either the inner or outer surface, or both. The lenses may also be fabricated using materials having different refractive indices for the near and far vision regions.

I claim:

1. A multifocal lens adapted for intraocular implantation in a human eye comprising a one piece transparent lens body having a substantially circular central region having a first optical power; and a plurality of concentric ring regions coaxially surrounding said central region having second and third optical powers both different from said first optical power, the innermost of said ring regions having a second optical power, and each subsequent ring region having an optical power different from the optical power of the ring region immediately inward therefrom, with the proviso that said plurality of concentric ring regions include either at least one ring region having said first optical power, or at least two ring regions which have the same power.

2. A lens according to claim 1, wherein the central region is powered for near vision.

3. A lens according to claim 1, wherein the central region and ring regions are sized such that over an average range of a patient's pupillary excursion about one-half of the exposed portion of the lens is powered for near vision.

4. A lens according to claim 1 wherein the central region is from about 1 to 3 mm in diameter.

5. A lens according to claim 4, wherein the concentric ring regions have a radial thickness of from about 0.125 mm to about 2 mm.

6. A lens according to claim 5, wherein the concentric ring regions all have equal area.

7. A lens according to claim 5, wherein the concentric ring regions all have equal radial thickness.

8. A lens according to claim 1, further comprising haptics for fixing the lens within the anterior or posterior chamber of the eye.

9. A lens according to claim 1, wherein the difference in effective power first, second and third optical powers is from about 1 to 3 diopters.

10. A multifocal lens adapted for intraocular implantation in a human eye comprising a one piece transparent lens body having a substantially circular central region having a first optical power; and a plurality of concentric ring regions coaxially surrounding said central region, the first innermost of said ring regions having a second optical power different from said first optical power, and a second subsequent ring region having a third optical power different from the optical power of the innermost ring region and different from the optical power of the central region.

11. A lens according to claim 10, including a third subsequent ring region having said first optical power.

12. A lens according to claim 10 including a third subsequent ring region having said second optical power.

13. A lens according to claim 12 including a fourth ring region having said third optical power.

14. A lens according to claim 10 having subsequent third, fourth and fifth ring regions respectively with said first, second and third optical powers.

15. A lens according to claim 10 wherein the central region is powered for near vision.

16. A lens according to claim 10 wherein said plurality of concentric ring regions are formed by at least one of lathe cutting, compression molding, injection molding, photoetching, milling or electro-forming.

17. A multifocal lens adapted for intracular implantation in a human eye comprising a one piece transparent lens body having a substantially circular central region having a first optical power; and a plurality of concentric ring regions coaxially surrounding said central region, the first innermost of said ring regions having a second optical power different from said first optical power, a second subsequent ring region having said first optical power, and a third subsequent ring region having a third optical power different from the optical power of the first and second ring regions.

18. A lens according to claim 17 including a fourth subsequent ring region having said first optical power.

* * * * *

UNITED STATES PATENT AND TRADEMARK OFFICE
CERTIFICATE OF CORRECTION

PATENT NO. : 5,158,572
DATED : October 27, 1992
INVENTOR(S) : James M. Nielsen

It is certified that error appears in the above-identified patent and that said Letters Patent is hereby corrected as shown below:

Drawings,
Sheets 1 and 2 of the drawings have been replaced by the attached Sheets 1 and 2, respectively.

Signed and Sealed this

Twenty-eighth Day of December, 2004

JON W. DUDAS
*Director of the United States Patent and Trademark Office*